United States Patent
Jacobs

(10) Patent No.: US 10,668,253 B2
(45) Date of Patent: Jun. 2, 2020

(54) METHODS FOR EXCHANGING DEVICES

(71) Applicant: TELEFLEX INNOVATIONS S.À.R.L., Luxembourg (LU)

(72) Inventor: Peter Jacobs, St. Louis Park, MN (US)

(73) Assignee: Teleflex Life Sciences Limited, Valletta (MT)

( * ) Notice: Subject to any disclaimer, the term of this patent is extended or adjusted under 35 U.S.C. 154(b) by 144 days.

(21) Appl. No.: 15/727,243

(22) Filed: Oct. 6, 2017

(65) Prior Publication Data

US 2019/0015637 A1    Jan. 17, 2019

Related U.S. Application Data

(63) Continuation-in-part of application No. 15/646,206, filed on Jul. 11, 2017.

(51) Int. Cl.
*A61M 25/06* (2006.01)
*A61M 25/00* (2006.01)
(Continued)

(52) U.S. Cl.
CPC .... *A61M 25/0662* (2013.01); *A61M 25/0021* (2013.01); *A61M 25/0169* (2013.01); *A61M 29/00* (2013.01); *A61M 2025/0687* (2013.01)

(58) Field of Classification Search
CPC ..... A61B 17/0057; A61B 2017/00623; A61M 2025/09116; A61M 2025/09125;
(Continued)

(56) References Cited

U.S. PATENT DOCUMENTS

| 5,059,183 A | 10/1991 | Semrad |
| 5,322,508 A * | 6/1994 | Viera ............... A61M 25/09 604/528 |

(Continued)

FOREIGN PATENT DOCUMENTS

| EP | 1163020 B1 | 9/2004 |
| EP | 1773438 B1 | 1/2017 |

(Continued)

OTHER PUBLICATIONS

Officer Gunter Held, International Search Report and the Written Opinion, International Patent Application PCT/US2017/013314, dated Apr. 18, 2017, 11 pp.

*Primary Examiner* — Katrina M Stransky
*Assistant Examiner* — Brigid K Byrd
(74) *Attorney, Agent, or Firm* — Offit Kurman, P.C.; Gregory A. Grissett

(57) ABSTRACT

A method for replacing a first sheath, whose distal end is positioned inside a vessel and whose proximal end is positioned outside the skin of a patient, with a second sheath may involve inserting a dilator over a guidewire and into the first sheath until a distal end of the dilator and a distal end of the guidewire are positioned inside the vessel. The dilator may be hubless or include a removable hub, and may define an external channel configured to receive a second guidewire. The method may further involve removing the first sheath, thereby leaving the dilator and the guidewire in place. After removing the first sheath, a second sheath may be passed over the dilator and the guidewire until the distal end of the second sheath is positioned inside the vessel. The method may further involve removing the dilator and the guidewire, leaving the second sheath in place.

17 Claims, 16 Drawing Sheets

(51) Int. Cl.
*A61M 29/00* (2006.01)
*A61M 25/01* (2006.01)

(58) Field of Classification Search
CPC .. A61M 2025/0177; A61M 2025/0183; A61M 25/0169; A61M 25/0172; A61M 25/06–0693; A61M 2025/1056
See application file for complete search history.

(56) References Cited

U.S. PATENT DOCUMENTS

| | | | |
|---|---|---|---|
| 5,363,847 A | 11/1994 | Viera | |
| 6,010,520 A | 1/2000 | Pattison et al. | |
| 6,245,054 B1 * | 6/2001 | Fuimaono | A61M 25/0017 600/585 |
| 7,094,209 B2 | 8/2006 | Egnelöv et al. | |
| 8,097,007 B2 | 1/2012 | Evans et al. | |
| 8,435,256 B2 | 5/2013 | von Lehe et al. | |
| 9,675,371 B2 | 6/2017 | Shimon et al. | |
| 2004/0138674 A1 * | 7/2004 | Egnelov | A61B 17/0057 606/108 |
| 2004/0147950 A1 | 7/2004 | Mueller, Jr. et al. | |
| 2006/0217664 A1 * | 9/2006 | Hattler | A61M 25/0668 604/164.1 |
| 2009/0137870 A1 | 5/2009 | Bakos et al. | |
| 2009/0318894 A1 * | 12/2009 | Lafitte | A61M 25/0668 604/528 |
| 2011/0208222 A1 | 8/2011 | Ljahnicky et al. | |
| 2012/0165854 A1 * | 6/2012 | Pipenhagen | A61B 17/0057 606/191 |
| 2012/0296275 A1 * | 11/2012 | Martin | A61M 29/00 604/103.05 |
| 2013/0025588 A1 | 1/2013 | Bosel et al. | |
| 2014/0039264 A1 | 2/2014 | Heiman et al. | |
| 2014/0309686 A1 | 10/2014 | Ginn et al. | |
| 2016/0228109 A1 | 8/2016 | Jacobs et al. | |
| 2017/0135725 A1 | 5/2017 | Tegels | |
| 2019/0015204 A1 | 1/2019 | Jacobs | |
| 2019/0110781 A1 | 4/2019 | Walters et al. | |

FOREIGN PATENT DOCUMENTS

| | | |
|---|---|---|
| WO | 9214396 A1 | 9/1992 |
| WO | 20150099977 A1 | 7/2015 |
| WO | 2017123853 A1 | 7/2017 |

* cited by examiner

METHODS FOR EXCHANGING DEVICES

CROSS-REFERENCE TO RELATE APPLICATION

This application is a continuation-in-part of pending U.S. application Ser. No. 15/646,206, filed Jul. 11, 2017, entitled "METHODS FOR EXCHANGING DEVICES," the entirety of which is hereby incorporated by reference for all purposes.

TECHNICAL FIELD

This application relates generally to methods for exchanging devices during vascular procedures. Implementations involve, but are not limited to, the exchange of devices such as sheath devices, including using a guidewire and a dilator configured to pass over the guidewire.

BACKGROUND

Percutaneous procedures often involve accessing vasculature with elongated instruments, e.g., catheters, deployed in an ordered sequence. Common vasculature access points for such procedures include the femoral artery in a patient's groin area and the radial artery in the patient's forearm, each of which provides direct access to the central vasculature system, including the central venous system. Entry into the femoral and radial arteries is often accomplished via the Seldinger technique, which involves using a hollow needle to poke through a patient's skin, subcutaneous tissue and targeted vessel wall, thereby creating a puncture hole through each layer. After the needle poke, a guidewire is inserted through the needle until a distal end of the guidewire passes through the puncture hole and protrudes into the vessel lumen. The needle may then be removed and additional instrumentation inserted at the same access point into the vessel along the track provided by the guidewire.

Depending on the specific procedure being performed and the characteristics of the patient being operated on, procedural instrumentation may be inserted directly over the guidewire in the absence of an introducer assembly (also known as the "bareback method"). More commonly, however, an introducer assembly is first inserted over the guidewire and fed into the vessel. Such an assembly may include an introducer sheath having a hemostasis valve at its proximal end and coupled with a dilator having an integrated proximal hub. Once a distal portion of the introducer sheath is positioned within the vessel, the dilator is removed by disengaging its proximal hub from the sheath's hemostasis valve and pulling on the hub, leaving the sheath and the guidewire in place to feed a guiding catheter into the vessel. The guiding catheter may be configured to channel a procedural device or assembly, such as a transcatheter aortic valve replacement ("TAVR") assembly, into and through the vessel to a desired treatment site. In such cases, deployment of the aortic valve replacement is followed by removal of the procedural assembly (minus the valve) and the guiding catheter, leaving the introducer sheath and guidewire in place.

Removal of the introducer sheath and guidewire would leave an exposed puncture hole in the vessel wall, causing internal and external bleeding. To avoid or minimize the effects of this result, the puncture hole created through the vessel wall must be sealed. A common method of controlling the puncture hole is to maintain external pressure (e.g., human hand pressure) over the vessel until the puncture seals by natural clot formation processes. This method of puncture closure typically takes between 30 and 90 minutes, can be uncomfortable for the patient, can result in excessive restriction or interruption of blood flow, and can consume costly time and effort on the part of the hospital staff. Another method of controlling the puncture hole is to implant a sealing device or assembly over the puncture. This method can involve exchanging the procedural introducer sheath with a second, different-sized introducer sheath configured specifically for guiding the sealing device or assembly to the vessel.

SUMMARY

Some existing methods of exchanging the procedural introducer sheath with the second, different-sized introducer sheath rely solely on the guidewire to channel the second introducer sheath to the vessel and through the puncture hole. The procedural introducer sheath is pulled proximally over the guidewire, and then the second introducer sheath is inserted over the guidewire. The present inventor recognizes that these methods, however, increase the risk of losing the original vessel access point due to a guidewire lacking sufficient stiffness to support the second introducer sheath or movement of the guidewire, an outcome more likely when operating on patients who may have a thicker layer of fat tissue between the targeted vessel and the skin. Additionally, these methods can be associated with excessive patient blood loss due to the small cross-sectional size of the guidewire relative to the puncture hole. Other methods, such as that disclosed in U.S. Pat. No. 7,094,209, which is incorporated by reference herein in its entirety, utilize a stiff, lumenless guide rod in lieu of a guidewire to facilitate sheath exchange. The present inventor further recognizes that such methods, however, are vulnerable to vessel perforation since the guide rod's distal end cannot track to a parallel orientation relative to the vessel wall through advancement over a guidewire. They also increase the risk of losing the vessel access point due to the typically short length of the guide rod. There is thus a need in the art for apparatuses and methods configured to exchange vascular sheaths while maintaining the original vessel access point and without perforating the vessel wall.

In some embodiments, a method for replacing a first sheath, whose distal end is positioned inside a vessel and whose proximal end is positioned outside the skin of a patient, with a second sheath may involve inserting a dilator over a guidewire and into the first sheath until a distal end of the dilator and a distal end of the guidewire are positioned inside the vessel. The method may further involve removing the first sheath, thereby leaving only the dilator and the guidewire in place; passing the second sheath over the dilator and the guidewire until a distal end of the second sheath is positioned inside the vessel; and removing the dilator and the guidewire, thereby leaving only the second sheath in place.

In some examples, the dilator may be hubless or include a removable hub (in each case herein where the dilator is referred to as hubless or including a removable hub, the dilator may be one, the other, or both) and may define a lumen configured to receive the guidewire. In some embodiments, the dilator may include a middle portion having an approximately constant diameter. A portion of the distal end of the dilator and a proximal end of the dilator may be tapered. In some examples, the tapered portion of the distal end of the dilator may include a radiopaque band. In some examples, multiple portions of the dilator include a radiopaque element (e.g., radiopaque filler material impregnated into a polymer of the dilator portions). In some embodiments, the diameter of the middle portion of the dilator may be approximately the same size as a puncture hole in the vessel wall created during a vascular procedure. The dilator may be of any desired length. In some examples, the dilator may be about 30 cm to about 70 cm long, inclusive. In some embodiments, the dilator may have an approximately uniform stiffness profile along its length.

In some examples, the first sheath may be a procedural introducer sheath configured to channel at least one interventional device to the vessel. The interventional device may include a transcatheter aortic valve replacement assembly in some implementations. In some examples, the second sheath may be a sealing introducer sheath configured to channel an implant assembly to the vessel. The implant assembly may be configured to seal the puncture hole created in a wall of the vessel during the vascular procedure.

In some embodiments, the guidewire may define a lumen and a length that is greater than the length of the dilator. In some examples, the length of the guidewire may be about 30 cm to about 80 cm, inclusive. In some embodiments, the distal end of the guidewire may extend at least about 5 cm or at least about 10 cm within a lumen of the vessel after placement therein. In some examples, an external diameter of the guidewire may be about 0.01 inches to about 0.04 inches, inclusive. In various implementations, the vessel may comprise a portion of the femoral artery or the radial artery. In some examples, the distance between an outer surface of the vessel wall and the skin of the patient may be about 1 cm to about 10 cm.

In some examples, the dilator may define an external channel configured to slidably receive a channel guidewire. In some embodiments, upon removing the first sheath, the channel guidewire may remain inserted or seated within the external channel defined by the dilator. In some examples, passing the second sheath over the dilator and the guidewire may further comprise removing the channel guidewire from the external channel using the second sheath. In some embodiments, removing the dilator and the guidewire may further comprise leaving the channel guidewire in place within the patient. In some embodiments, a portion of the distal end of the dilator and a proximal end of the dilator may be tapered and the external channel may extend onto the distal and proximal ends. The guidewire and the channel guidewire may be substantially equally dimensioned in some embodiments.

BRIEF DESCRIPTION OF THE DRAWINGS

In the drawings, like numerals can be used to describe similar features and components throughout the several views. The drawings illustrate generally, by way of example but not by way of limitation, various embodiments discussed in this patent document.

Figure 1:
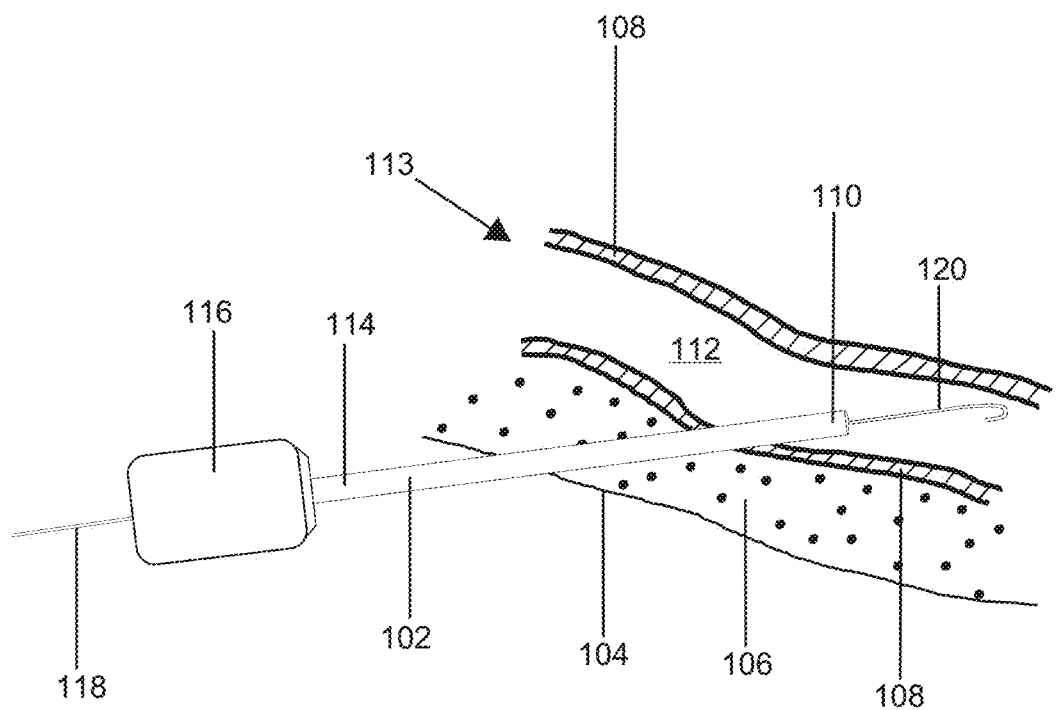
FIGS. 1-5 are schematic illustrations of steps in a sheath exchange process in accordance with embodiments of the present teachings.

The drawing figures are not necessarily to scale. Certain features and components may be shown exaggerated in scale or in schematic form, and some details may not be shown in the interest of clarity and conciseness.

DETAILED DESCRIPTION

Definitions

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document.

The terms "distal" and "proximal" refer to a position or direction relative to a treating clinician. "Distal" and "distally" refer to a position that is distant, or in a direction away, from the clinician. "Proximal" and "proximally" refer to a position that is closer to, or in a direction toward, the clinician.

The term "patient" refers to a mammal and includes both humans and animals.

All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Example Applications of the Present Teachings

Vascular procedures are performed throughout the world and require access to a blood vessel of the vasculature system through a puncture. FIGS. 1-5 and 9-13 include schematic illustrations of a puncture in a wall of a blood vessel (e.g., a femoral or radial artery or a desired vein or other vessel). The vessel is shown in cross-section passing beneath the skin and subcutaneous tissue of a patient. The vessel has been accessed by way of a percutaneous surgical procedure, which has resulted in an access path consisting of a tissue tract and the puncture. For example, the tract and puncture may have been formed by inserting an introducer assembly into a lumen of the vessel.

The present methods and systems can be used to exchange sheaths used in percutaneous procedures to introduce catheters and other intravascular devices into the vasculature. More particularly, disclosed methods and systems involve using at least one guidewire and a hubless or removable-hubbed, over-the-wire dilator to facilitate the exchange of various sheath devices while maintaining a vascular access point and avoiding vessel wall perforation. Some embodiments can involve the use of a hubless or removable-hubbed dilator that defines an external channel configured to receive a channel guidewire in addition to an axial guidewire received within a dilator lumen. Specific examples may involve the replacement of a procedural sheath, such as an introducer sheath for a TAVR assembly, with an introducer sheath configured to receive a vessel wall sealing assembly and/or implant; however, the methods disclosed may be readily applicable to a wide range of sheath devices employed during a wide range of vasculature procedures. Additional procedures requiring introducer sheaths include, for example, mitral valve repair or replacement, tricuspid valve repair or replacement, abdominal aortic aneurysm repair, thoracic aneurysm repair, transcutaneous aortic valve implantation ("TAVI"), endovascular aneurysm repair ("EVAR"), trans-septal occluder implantation and implantation of a variety of percutaneous ventricular-assist devices.

Sheath Exchange Methods, Systems and Devices:

FIG. 1 depicts a cross-sectional view of a blood vessel and surrounding tissue at the starting point of an example method described herein. As shown, a first sheath 102 has been inserted through an access path into the blood vessel of a patient. The access path, and thus the first sheath 102 inserted therethrough, extends through the skin 104, subcutaneous tissue 106, and blood vessel wall 108, such that a distal end 110 of the first sheath protrudes into a lumen 112 of the blood vessel 113 through a puncture hole in the vessel wall. Opposite the distal end 110, the first sheath 102 includes a proximal end 114 having a hemostasis valve 116, both external to the patient. As further shown, a first, axial guidewire 118 may be positioned within the first sheath 102 such that a distal end 120 of the guidewire protrudes from the distal end 110 of the sheath into the lumen 112 of the blood vessel 113.

The particular size and configuration of the first sheath 102 may vary according to the specific intravascular procedure being performed. For example, the first sheath may be a procedural introducer sheath used to facilitate the insertion and removal of one or more surgical instruments, e.g., a guiding catheter, employed during a procedure. The first sheath may reduce lateral and axial movement of the guiding catheter used during a vascular procedure relative to the blood vessel wall, thereby reducing or eliminating vessel spasm. Particular embodiments may include an introducer sheath configured to feed a TAVR assembly through the vessel puncture hole. The length of the first sheath may vary depending on the depth of the targeted vessel 113 relative to the skin 104, said depth ranging from about 1 cm to about 10 cm in some embodiments, or depths less or greater than this range. The first sheath defines a lumen, the diameter of which may also vary, configured to receive various elongated vascular instruments. While the first sheath 102 shown in FIG. 1 is generally cylindrical, any cross-section may be used (and the cross-section can vary along the length), and the shape of the sheath may also vary, defining converging and/or asymmetrical tip portions, for example.

The size and configuration of the guidewire 118 may also vary. In some examples, a hollow guidewire defining a lumen may be used. In other embodiments, the guidewire may be solid. The diameter of the guidewire may vary depending on the diameter of the vessel lumen 112 and/or the diameter of the other instruments employed during the operation. Specific embodiments may include a guidewire having a diameter ranging from about a 0.01 in. to about 0.04 in., about 0.013 in. to about 0.038 in., about 0.015 in. to about 0.02 in., or about 0.018 in. The length of the guidewire may also vary, including ranging from about 30 cm to about 270 cm, about 30 cm to about 80 cm, about 30 cm to about 70 cm, about 35 cm to about 45 cm, or about 55 cm to about 65 cm in various embodiments. Guidewires may have a length about twice as long as the dilator 122 shown in FIG. 2, for example. In some examples, the guidewire may define a tapered tip portion at the distal end, which may also be curved to avoid perforation of the vessel wall 108. The guidewire 118 may comprise stainless steel in some embodiments. It is to be appreciated that the dimensions in this paragraph, and in this document, are exemplary only, and any suitable dimensions may be used.

Figure 2:
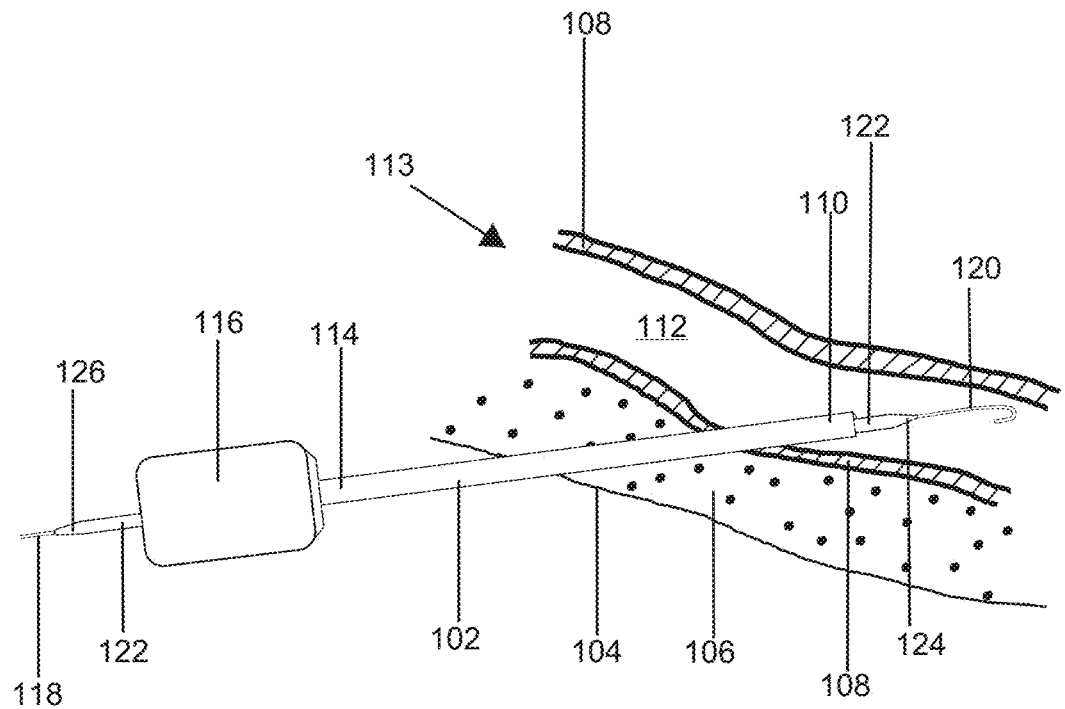

FIG. 2 depicts a subsequent step, prior to removing the first sheath 102 from the access path. At this stage, a dilator 122 may be inserted over the guidewire 118 and through the lumen of the first sheath 102, such that a distal end 124 of the dilator protrudes into the vessel lumen 112, along with the distal end 120 of the guidewire. A proximal end 126 of the dilator 122 may protrude outside the patient's skin 104, beyond the proximal end 114 of the first sheath 102. The dilator 122 may facilitate exchange of the first sheath 102 with a second sheath, and may thus be referred to as an "exchange dilator." After placement of the dilator 122 over the guidewire 118, the guidewire may protrude beyond the distal end of the dilator, extending into the lumen 112, such as at a distance of about 3 cm to about 10 cm or another desired amount. This extension of the guidewire beyond the dilator may prevent the dilator 122 from perforating the inner vessel wall, as further distal advancement of the dilator over the guidewire 120 will result in the distal end 124 of the dilator following the track of the guidewire and away from the blood vessel wall 108. With the dilator 122 and guidewire 118 in place, the first sheath 102 may be removed.

The size and configuration of the dilator 122 may vary. The dilator 122 may be hubless in some examples. The dilator 122 may include a removable hub in other examples. The dilator 122 may also define an internal lumen configured to receive the guidewire 118, thus configuring the dilator to pass over the guidewire during its insertion and removal. In one embodiment, the dilator is both hubless and configured to pass over the guidewire 118. The dilator generally defines two ends: the distal end 124 configured for insertion into the vessel lumen 112, and the proximal end 126 configured to remain outside of a patient's skin 104. In one embodiment, both the distal end 124 and the proximal end 126 define a tapered portion, such that the width of each end narrows to define an open tip. The tapered portion at the distal end 124 may facilitate passage into the lumen 112, while a proximal tapered portion may ease sheath exchange.

Figure 3:
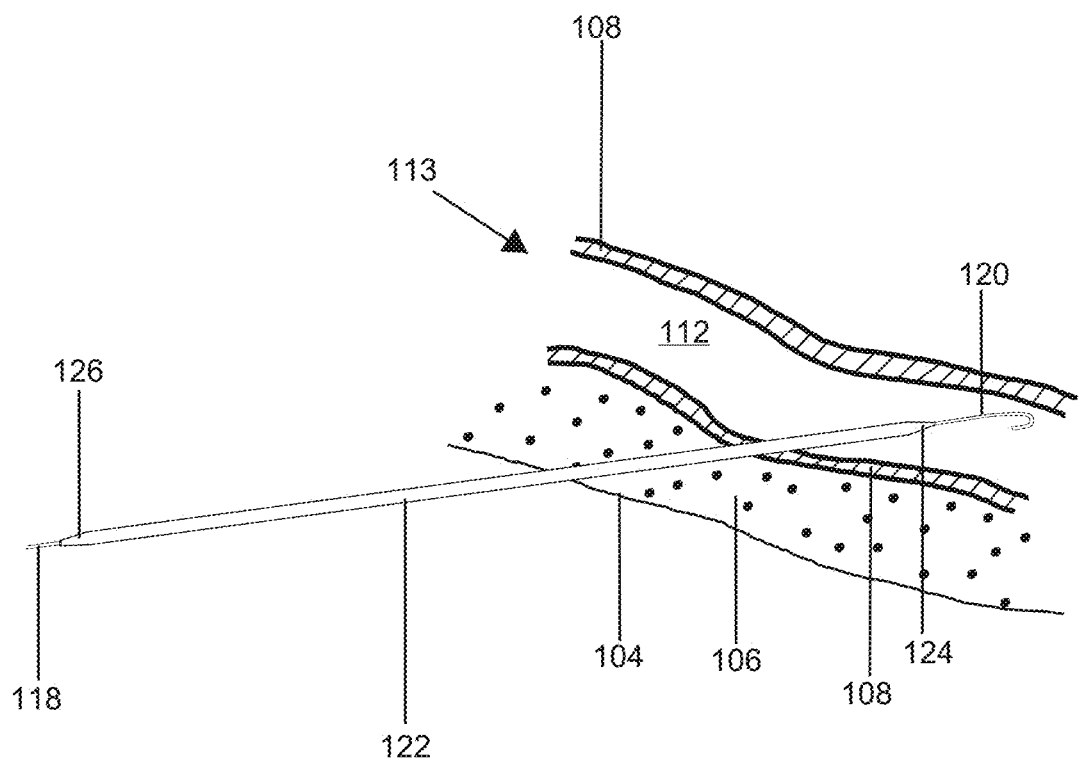

FIG. 3 shows a subsequent step, after removal of the first sheath 102, which may leave only the guidewire 118 and the dilator 122 inserted at the vessel access point. The distal ends 120, 124 of the guidewire and dilator, respectively, remain inserted within the lumen 112. Without the structural support provided by the first sheath 102, the dilator and guidewire, together, may maintain a reliable connection to the vessel access point through the original puncture hole. The guidewire 118, in particular, may serve as an anchor to the access point by protruding a sufficient distance within the lumen 112. In some examples, the guidewire 118 may extend about 4 cm to about 14 cm, about 6 cm to about 12 cm, or about 8 cm to about 10 cm within the lumen 112. By contrast, the first sheath 102 may extend a different amount, or a lesser amount, such as about 2 cm to about 8 cm within the lumen 112. Consistent placement of the guidewire 118 at the access point may thus provide a safety net that reduces the likelihood of losing the access point in the vessel, even upon movement of the guidewire and even in the absence of intravascular anchoring traditionally achieved via a curved distal end on one or more of the other instruments employed during a vascular procedure. This may be advantageous, as relocating the access point can be difficult, especially when operating on patients that have relatively large amounts of fat tissue between the skin 104 and the targeted blood vessel 113. In some embodiments, the width of the fat tissue contained between the skin 104 and the outer surface of the vessel wall 108 (opposite the lumen) may range from about 0.5 cm to about 15 cm, about 1 cm to about 10 cm, or about 5 cm to about 7 cm. In addition, the guidewire 118 provides a track for additional instruments to follow, thereby preventing or at least reducing the likelihood of such instruments perforating the vessel wall 108.

Figure 4:
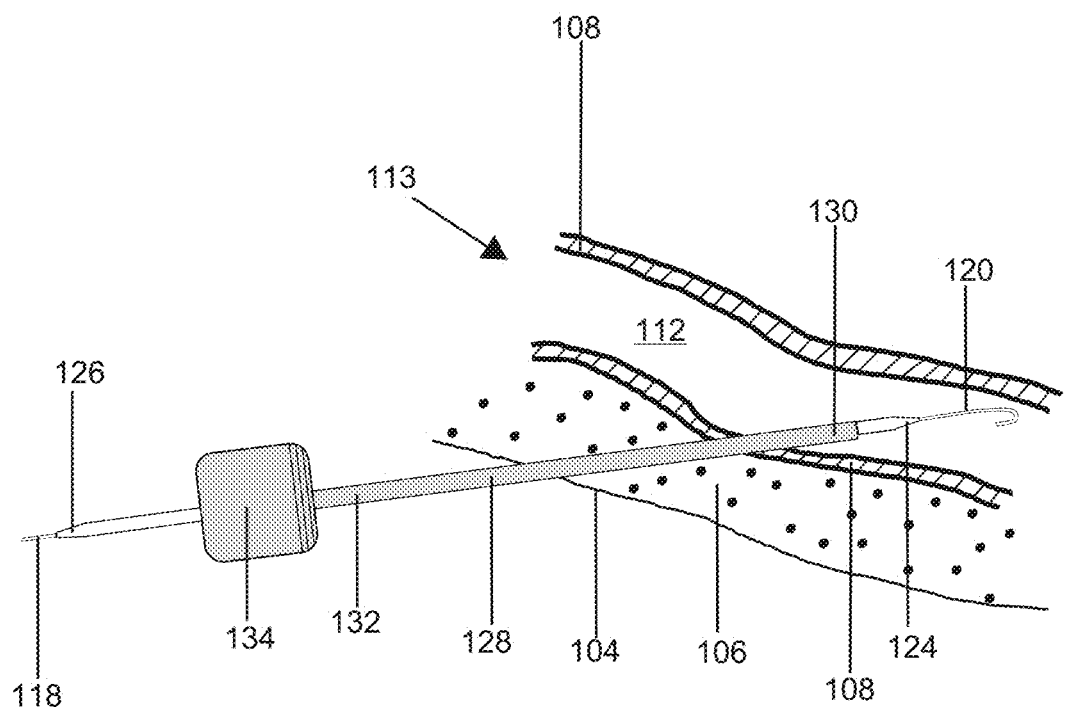

FIG. 4 shows a subsequent step, during which a second sheath 128 is inserted over the dilator 122 and the guidewire 118. The second sheath 128 includes a distal end 130 and a proximal end 132 having a hemostasis valve 134. The second sheath 128 may be inserted until its distal end 130 protrudes within the lumen 112. Like the first sheath 102, the second sheath 128 may protrude any desired amount, such as about 2 cm to about 8 cm, within the lumen 112. Because the dilator 122 is hubless or includes a removable hub, the dilator may remain inserted through the puncture hole while the second sheath 128 is inserted thereon. With the second sheath 128 in place, the guidewire 118 and the dilator 118 may be removed.

Figure 5:
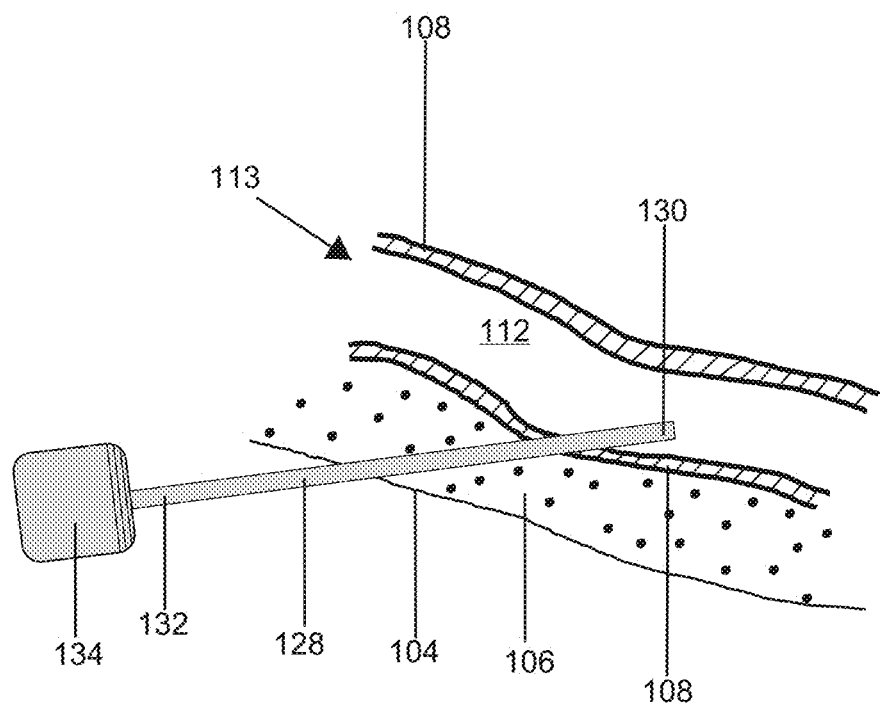

FIG. 5 shows a subsequent step, after removing the guidewire 118 and the dilator 122. At this stage, only the second sheath 128 remains inserted through the access path. With the second sheath 128 in place, various instruments may be directed into the blood vessel 113. The specific configuration of the second sheath 128 may vary. In some examples, the second sheath 128 may be used to facilitate the introduction of a sealing assembly, device and/or implant used to seal the puncture hole in the blood vessel wall 108 created during the vascular procedure. For example, the second sheath 128 may be an introducer sheath configured to receive and insert an implant assembly configured to seal the puncture hole. An example of such an implant assembly and introducer sheath is disclosed in U.S. Patent Application Publication No. 2016/0228109 to Jacobs et al., the contents of which are incorporated by reference in their entirety herein. The implant assembly may be used to seal various puncture sizes, including small, medium and large punctures resulting from 8F to 24F introducer sheaths, for example. In some embodiments, the second sheath 128 may comprise an integrated part of a tool used to seal the puncture hole. For tracking the distal placement of the second sheath 128, a radiopaque marker band may be embedded or otherwise attached to the sheath.

Figure 6:
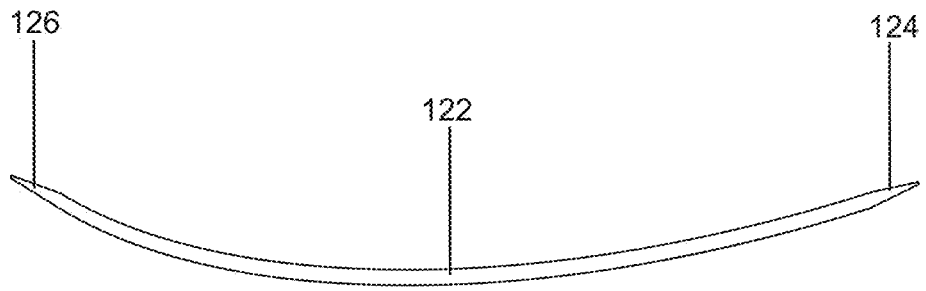
FIG. 6 is a schematic illustration of a dilator used in a sheath exchange process in accordance with embodiments of the present teachings.

FIG. 6 illustrates the dilator 122 used in an embodiment of the sheath exchange process described herein. The dilator 122 shown is hubless and defines two tapered ends 124, 126. In this specific example, both ends 124, 126 are identical or nearly identical. In other embodiments, the distal end 124 may be different than the proximal end 126 to any desired extent. For example, the distal end 124 may include a pre-formed curve. In some embodiments, the dilator 122 includes a straight, linear configuration from its proximal end 126 to its distal end 124. The dilator 122 defines an internal lumen that spans the length of the dilator for insertion of a guidewire therethrough. The external diameter of the dilator 122 must be small enough to fit within the lumen of the targeted blood vessel, and the inner diameter must be large enough to accommodate passage of a guidewire therethrough. In some embodiments, the middle portion of the dilator 122, i.e., excluding the tapered ends, may have an approximately constant outer diameter, which may be approximately equal to the diameter of the puncture hole defined by the vessel wall 108. In some examples, the outer diameter of the dilator 122 may range from about 0.04 in. to about 0.50 in., about 0.05 in. to about 0.46 in., about 0.07 in. to about 0.32 in., about 0.08 in. to about 0.12 in. The inner diameter defining the lumen of the dilator, including at the tapered ends, may range from about 0.02 in. to about 0.04 in., about 0.02 in. to about 0.03 in., or about 0.025 in. to about 0.038 in. In some examples, the length of the dilator may be greater than the length of the sheaths exchanged according to the processes described herein. For example, in some embodiments, the dilator 122 may have a length ranging from about 20 cm to about 70 cm, about 30 cm to about 60 cm, or about 35 cm to about 50 cm. In some embodiments, the dilator 122 may be customized to be at least about twice as long as the first sheath 102 and/or the second sheath 128. The length of the dilator may vary depending on the specific operation being performed and/or the patient receiving the operation.

The materials comprising the dilator 122 may vary. For example, the dilator 122 may comprise polyethylene and barium sulfate. In some embodiments, the dilator may comprise HDPE, Teflon, and/or Pebax, other materials, or combinations of these. The dilator 122 may also include a radiopaque material, e.g., a radiopaque band ranging in length from about 3 mm to about 15 mm. The radiopaque material may be positioned at or near the distal tip of the dilator to increase visibility of the distal end during placement within the blood vessel lumen. A radiopaque tip portion may comprise polyethylene with tungsten. The dilator may also be coated with a lubricating material, such as silicone, to facilitate insertion and removal through the access path and/or one or more introducer sheaths. The dilator 122 in the embodiment shown has a uniform stiffness profile. In some embodiments, one or more portions of the dilator, e.g., the distal portion, may have a variable flexibility. For example, a dilator may include a relatively flexible portion at or near one or both ends. In some examples, only one or even zero ends are tapered. Ends not defining a tapered portion may be bluntly shaped. The ends of the dilator may not be pre-bent in some embodiments, including the embodiment shown. In some examples, the dilator further comprises a measurement scale.

Figure 7:
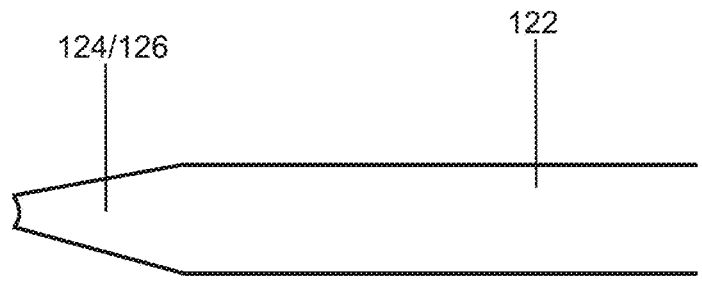
FIG. 7 is a schematic illustration of a magnified view of an end portion of the dilator shown in FIG. 6.

FIG. 7 is a schematic illustration of a magnified view of an end portion (124 or 126) of the dilator shown in FIG. 6. As shown, each end may be tapered to define a tip portion.

Figure 8A:
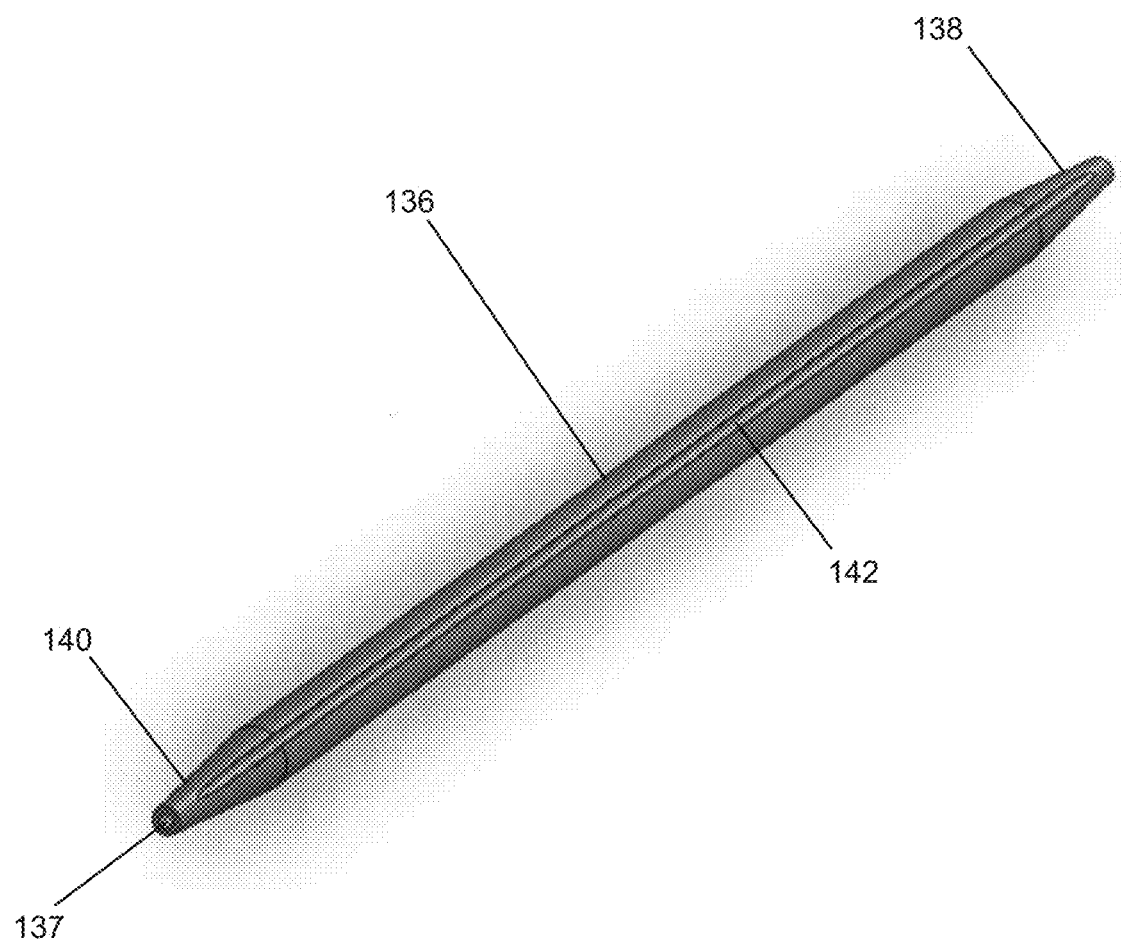
FIG. 8A is a schematic illustration of a dilator defining an external channel, which may be used in a sheath exchange process in accordance with embodiments of the present teachings.

FIG. 8A is a schematic illustration of another dilator 136 used in an embodiment of a sheath exchange process described herein. Like the dilator 122 shown in FIG. 6, dilator 136 defines an inner lumen 137 configured to receive an axial guidewire, e.g., guidewire 118, and a distal end 138 generally opposite a proximal end 140; however, the dilator 136 also defines an external channel 142 extending longitudinally along the length or a portion of the length of the dilator. The channel 142 can be configured to slidably receive a second guidewire during a sheath exchange process, such that the received guidewire rests within the channel 142. At certain moments in various sheath exchange processes, a channel guidewire may rest between the channel 142 and the inner surface of a sheath, such as sheath 102. The channel 142 can have an approximately consistent depth along the length of the dilator 136, but can be shallower at the distal and proximal ends 138, 140, where the tapered shape of the dilator reduces the external diameter thereof. Despite defining the inwardly-protruding channel 142, the dilator 136 can maintain the same or similar diameter as the dilator 122 shown in FIG. 6. In various embodiments, the channel 142 can be configured to accommodate a guidewire having a diameter of about 0.038 inches. In some examples, the channel 142 may be configured to accommodate a guidewire having a diameter of about 0.01 in. to about 0.04 in., about 0.013 in. to about 0.038 in., about 0.015 in. to about 0.02 in., or about 0.018 in., or any other desired size guidewire.

Figure 8B:
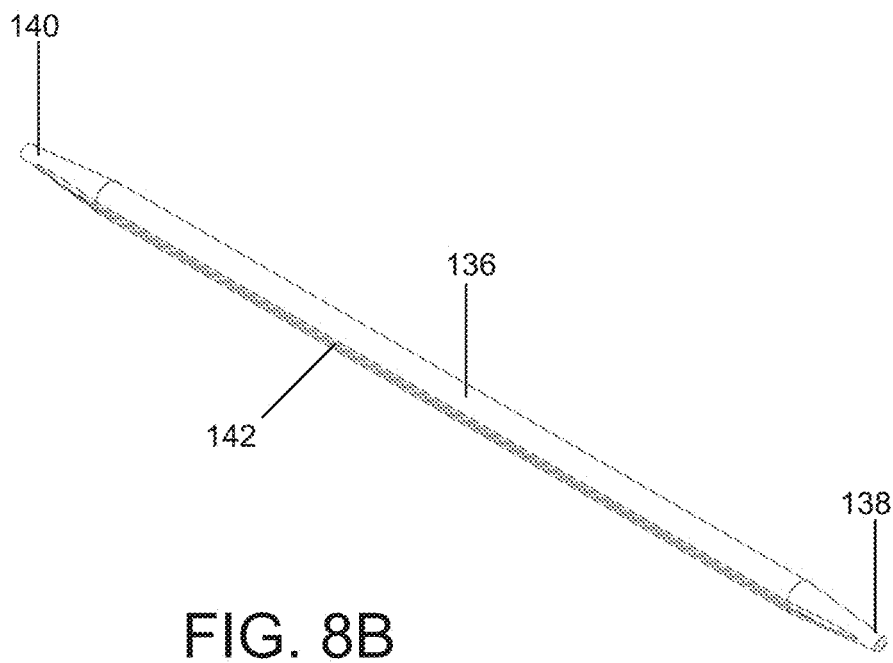
FIG. 8B is another schematic illustration of the dilator shown in FIG. 8A.

FIG. 8B is another schematic illustration of the dilator 136 shown in FIG. 8A. As shown, the channel 142 can define an elongate slot. When in use, the channel 142 can be oriented as desired by a user by rotating the dilator 136, such that the channel and guidewire resting therein are positioned in the manner necessary to exchange sheaths and/or perform an intravascular procedure.

Figure 8C:
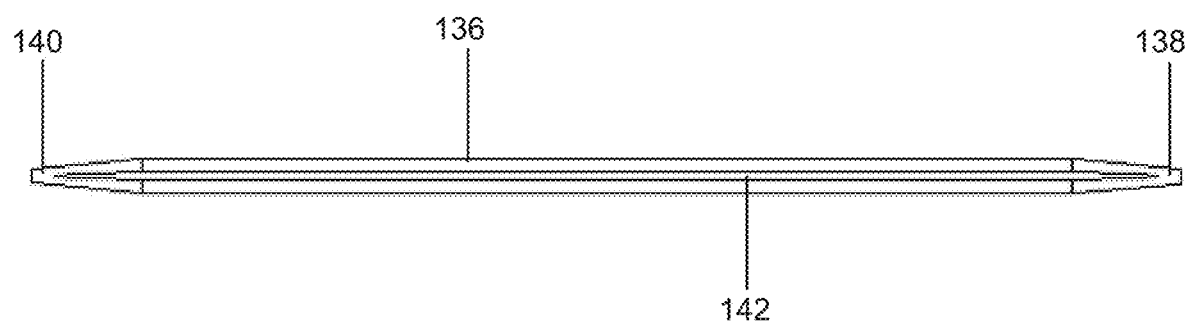
FIG. 8C is another schematic illustration of the dilator shown in FIG. 8A.

FIG. 8C is another schematic illustration of the dilator 136, shown in FIG. 8A, illustrating the full length of the channel 142 according to an embodiment, which can define rounded, pointed, squared or otherwise configured ends within the distal 138 and proximal 140 ends of the dilator.

Figure 9:
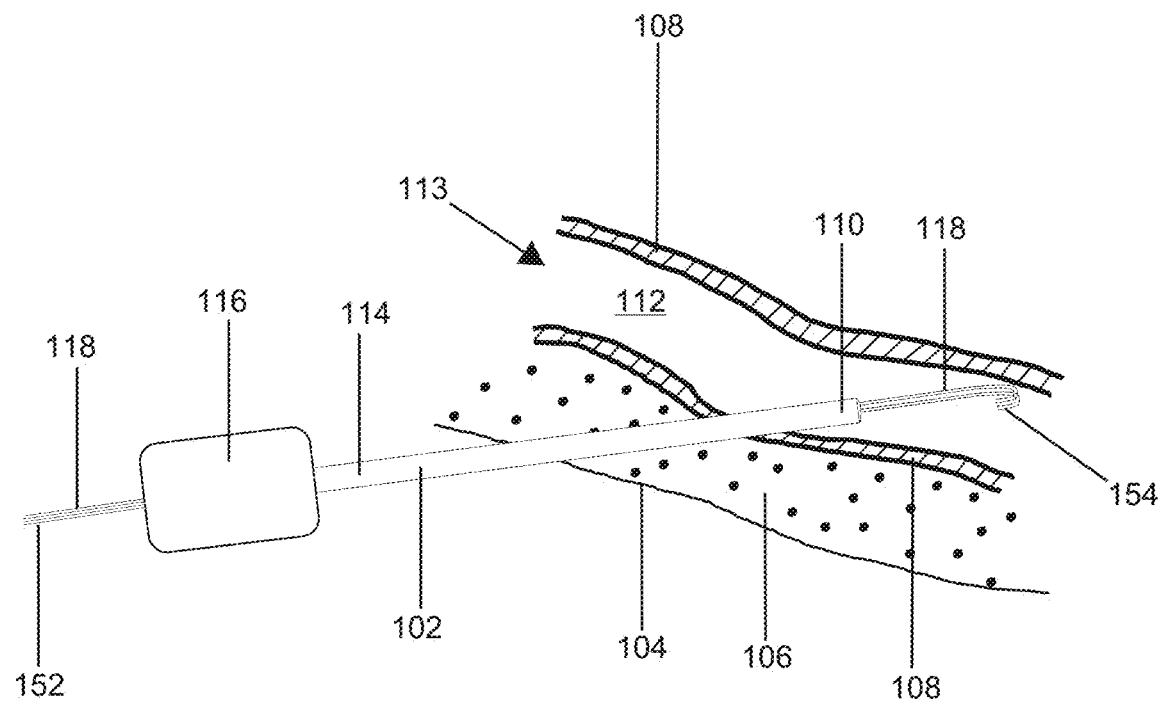
FIGS. 9-13 are schematic illustrations of steps in another sheath exchange process in accordance with embodiments of the present teachings.

FIG. 9 depicts a cross-sectional view of a blood vessel and surrounding tissue at the start of another example method described herein, showing the same anatomical features depicted in FIGS. 1-5. The first sheath 102 has been inserted through an access path, such that its distal end 110 protrudes into the lumen of the blood vessel. In addition to the first guidewire 118 positioned within the first sheath 102, a second, channel guidewire 152 has been positioned within the first sheath, such that its distal end 154 also protrudes into the lumen of the blood vessel. The size and configuration of the channel guidewire 152 may be the same or different than that of the first guidewire 118. In some examples, the channel guidewire 152 may have a diameter of about 0.038 in. Any other desired dimensions may be used.

Figure 10:
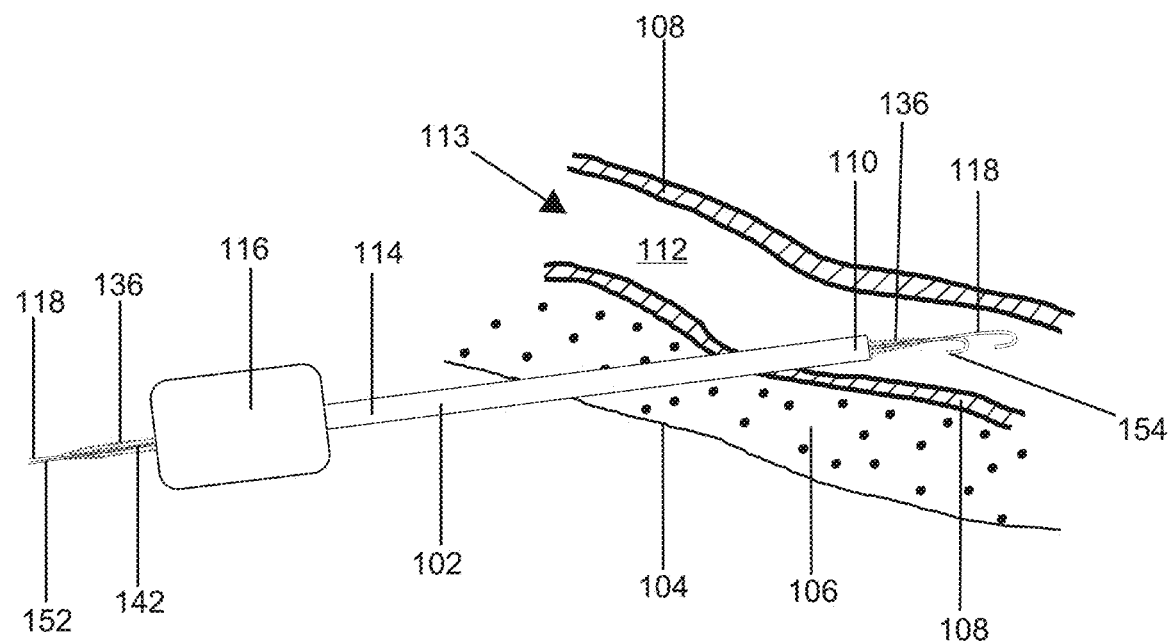

FIG. 10 depicts a subsequent step, prior to removing the first sheath 102 from the access path. At this stage, the dilator 136 may be inserted over the first guidewire 118, but not the channel guidewire 152, such that the channel guidewire slides within the channel 142 defined by the dilator 136. In this manner, the two guidewires 118, 152 may be separated along their lengths by a body portion of the dilator 136. In some examples, the dilator 136 can be inserted before the channel guidewire 152. According to such examples, a user can position a distal end of the channel guidewire 152 within the channel 142 defined by the dilator 136, and then proceed to slide the channel guidewire along the channel and through the access path.

Figure 11:
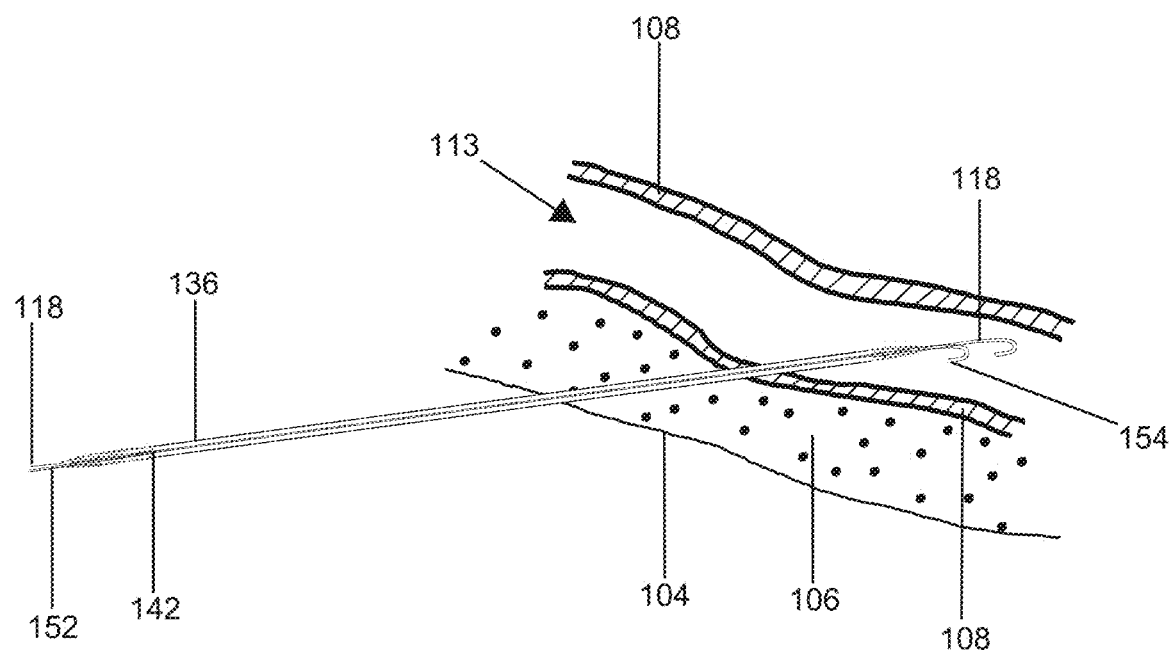

FIG. 11 depicts a subsequent step, after removal of the first sheath 102, which can leave the first guidewire 118 and the dilator 136 in the access path, along with the channel guidewire 152 coupled thereto.

Figure 12:
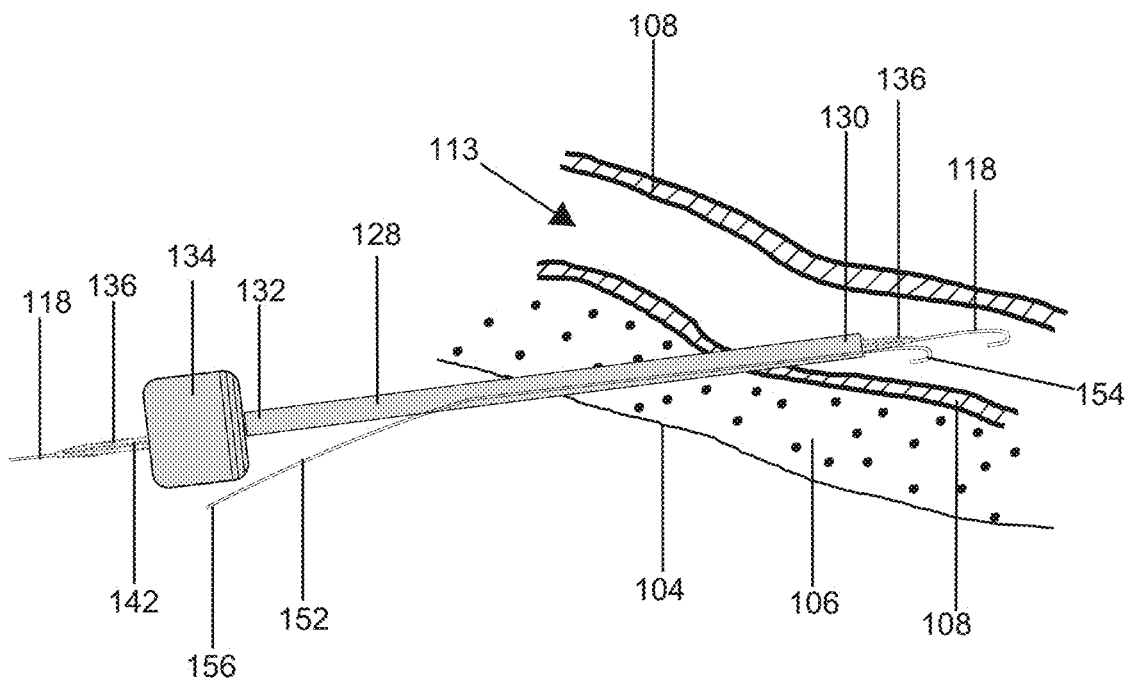

FIG. 12 shows a subsequent step, during which the second sheath 128 is inserted over the dilator 136 and the guidewire 118 running therethrough. As shown, the second sheath 128 can be used to dislodge the channel guidewire 152 from the dilator 136 in a snow plow like manner as the second sheath is inserted. To ensure proper separation of the channel guidewire 152 from the dilator 136, a user can first separate a proximal end 156 of the channel guidewire 152 from the dilator 136 prior to sliding the second sheath 128 over the dilator. As the sheath 128 is then moved along the dilator 136 toward the blood vessel 113, the tip of the sheath lifts the channel guidewire 152 wire out of the channel 142 so it lays outside of the sheath. In this manner, the second sheath 128 can serve as a wedge forced between the channel guidewire 152 and the dilator 136 until the two components are completely separated.

Figure 13:
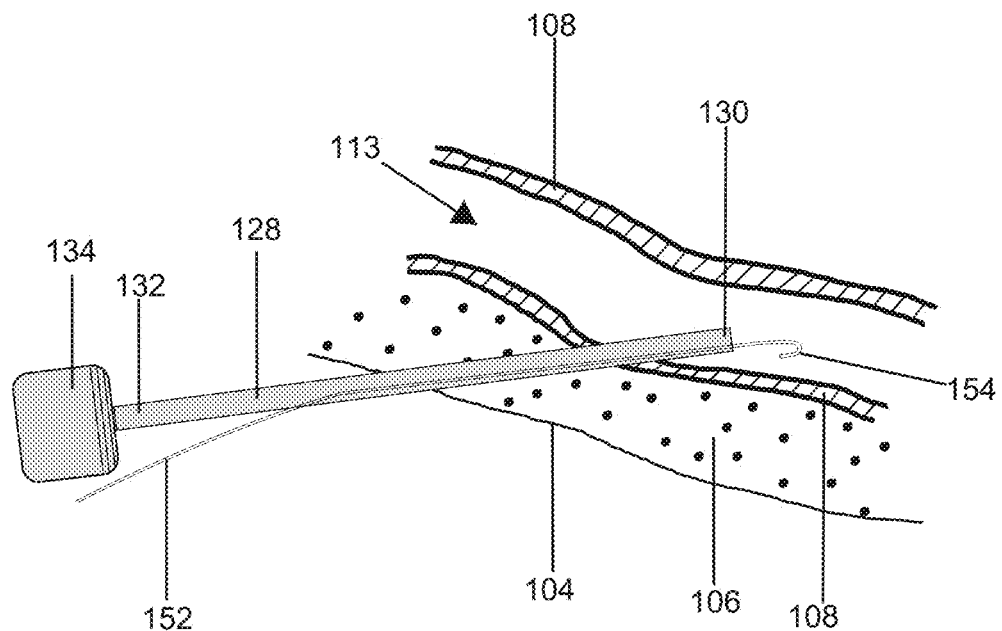

FIG. 13 shows a subsequent step, after which the dilator 136 and the first guidewire 118 have been removed, leaving only the channel guidewire 152 and second sheath 128. Leaving the channel guidewire 152 within the access path throughout the sheath exchange process depicted in FIGS. 9-13 ensures that the access path and vessel wall opening is not lost during an operation, thus providing an additional placeholder that may be especially desirable when large amounts of tissue, e.g., fat tissue, lie between the patient's skin and the targeted blood vessel.

Figure 14:
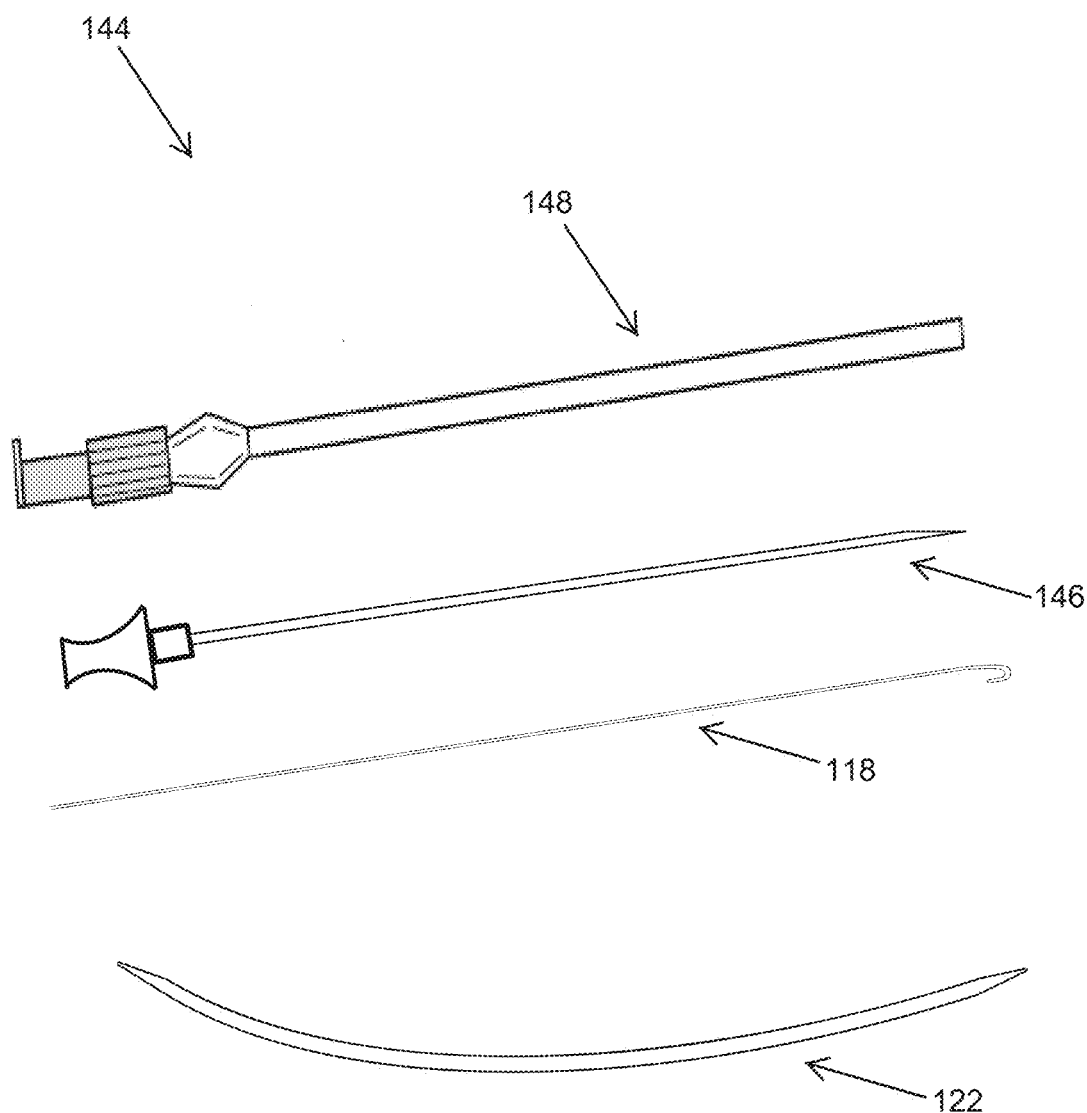
FIG. 14 is a schematic illustration of an introducer kit including an access needle, a dilator, a guidewire, and a delivery assembly used according to at least one embodiment of the present teachings.

Sheath Introducer Kits:

FIG. 14 is a schematic illustration of a sheath introducer kit used according to at least one embodiment disclosed herein. The introducer kit 144 may be referred to as a "micro-introducer kit" in some examples. The introducer kit 144 includes a guidewire 118, a dilator 122, an access needle 146, and a delivery assembly 148. The access needle 146, which may be echogenic or smooth, may also be hollow and is configured to create the access path and vessel wall puncture hole prior to insertion of the guidewire 118 or any other interventional device. The delivery assembly 148 may be coupled with one or more implant assemblies or devices, e.g., TAVR, TAVI, EVAR, and/or sealing assemblies, which may be preloaded if desired in some examples. Together, the components of the kit 135 may be employed to form an access path to a blood vessel, introduce one or more interventional devices thereto, and facilitate the exchange of one or more vascular sheaths for one or more separate vascular sheaths. Embodiments may include fewer or additional components as necessary to perform specific vascular procedures. For example, the kit 144 may also include an introducer sheath configured to feed the guidewire 118, dilator 122, and/or additional components to a blood vessel through the access path created by the needle 146.

Figure 15:
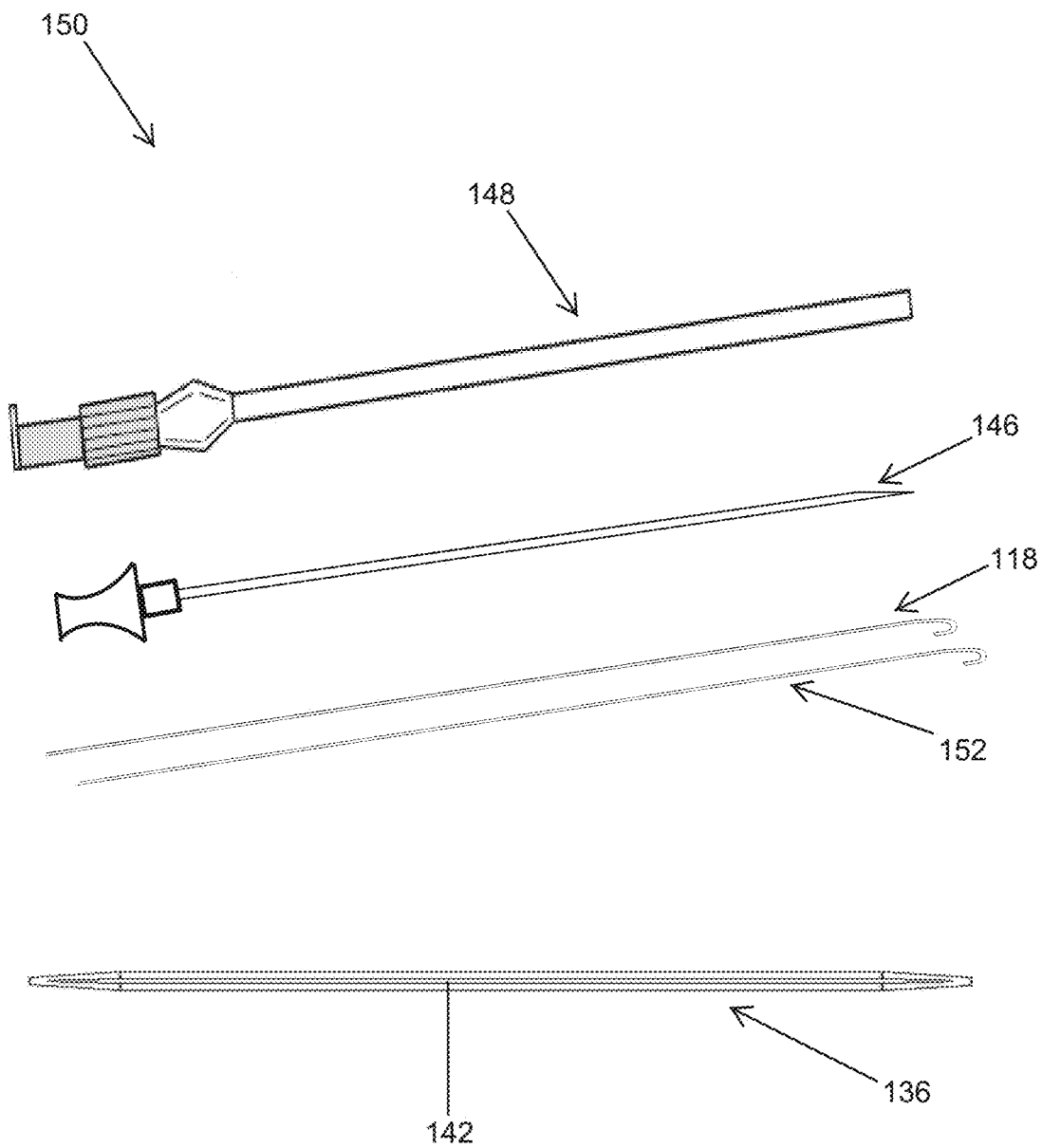
FIG. 15 is a schematic illustration of another introducer kit including an access needle, a dilator defining an external channel, two guidewires, and a delivery assembly used according to at least one embodiment of the present teachings.

FIG. 15 is a schematic illustration of another sheath introducer kit. The introducer kit 150 includes the same or similar delivery assembly 148, guidewire 118, and access needle 146 included in introducer kit 144, but with the dilator 136 shown in FIGS. 8A-8C and an additional channel guidewire 152 configured to be slidably inserted into the channel 142 defined by the dilator 136.

Notes and Examples

The present sheath exchange systems, devices, kits and methods can be used by a treating clinician during a vascular procedure. While applicable to any of a variety of patient types, the present systems, devices, kits and methods may be suited for performing vascular procedures on relatively heavy set or obese patients having a relatively thick layer of fat tissue between the skin and the targeted access point in a blood vessel wall. More tissue movement may occur in such patients during a vascular procedure. By simultaneously utilizing both a guidewire and an over-the-wire, hubless or removable-hubbed dilator, the present methods reduce the likelihood of losing the vessel access point and excessive blood compared to methods that only rely solely on the guidewire or a separate device, such as a guide rod. The sheaths and/or other interventional devices exchanged according to the present method may be small, medium or large in size.

The above Detailed Description includes references to the accompanying drawings, which form a part of the Detailed Description. The Detailed Description should be read with reference to the drawings. The drawings show, by way of illustration, specific embodiments in which the present systems, devices, kits and methods can be practiced. These embodiments are also referred to herein as "examples."

Although the present invention has been described with reference to certain embodiments, persons skilled in the art will recognize that changes may be made in form and detail without departing from the spirit and scope of the invention. For example, a wide variety of modifications to the embodiments of the present disclosure may be made with respect to, for example, the sequence of method steps and configuration of the percutaneous instruments employed during one or more of these steps.

The Detailed Description is intended to be illustrative and not restrictive. For example, the above-described examples (or one or more features or components thereof), can be used in combination with each other. Other embodiments can be used, such as by one of ordinary skill in the art upon reviewing the above Detailed Description. Also, various features or components have been or can be grouped together to streamline this disclosure. This should not be interpreted as intending that the unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a method for replacing a first sheath, whose distal end is positioned inside a vessel and whose proximal end is positioned outside the skin of a patient, with a second sheath can comprise inserting a dilator over a guidewire and into the first sheath until a distal end of the dilator and a distal end of the guidewire are positioned inside the vessel; removing the first sheath, thereby leaving the dilator and the guidewire in place; passing the second sheath over the dilator and the guidewire until a distal end of the second sheath is positioned inside the vessel; and removing the dilator and the guidewire, thereby leaving the second sheath in place.

In Example 2, the method of Example 1 can optionally further comprise inhibiting patient blood loss through a puncture hole in a wall of the vessel using the combination of the dilator and the guidewire to substantially fill the puncture hole.

In Example 3, the method of any one of Examples 1 or 2 can optionally be configured such that the dilator is hubless and defines a lumen configured to receive the guidewire.

In Example 4, the method of any one of Examples 1 or 2 can optionally be configured such that the dilator includes a removable hub and defines a lumen configured to receive the guidewire.

In Example 5, the method of any one or any combination of Examples 1-5 can optionally be configured such that the dilator comprises a middle portion having an approximately constant diameter, and a portion of the distal end of the dilator and a proximal end of the dilator are tapered.

In Example 6, the method of Example 5 can optionally be configured such that the tapered portion of the distal end of the dilator comprises a radiopaque band.

In Example 7, the method of Example 5, wherein one or more portions of the dilator include a radiopaque element.

In Example 8, the method of Example 5 can optionally be configured such that the diameter of the middle portion of the dilator is approximately the same size as a puncture hole in a wall of the vessel.

In Example 9, the method of any one or any combination of Examples 1-8 can optionally be configured such that the dilator is about 30 cm to about 70 cm long, inclusive.

In Example 10, the method of any one or any combination of Examples 1-9 can optionally be configured such that the dilator comprises an approximately uniform stiffness profile along a length of the dilator.

In Example 11, the method of any one or any combination of Examples 1-10 can optionally be configured such that the first sheath is a procedural introducer sheath configured to channel at least one interventional device to the vessel.

In Example 12, the method of Example 11 can optionally be configured such that the interventional device comprises a transcatheter aortic valve replacement assembly.

In Example 13, the method of any one or any combination of Examples 1-12 can optionally be configured such that the second sheath is a sealing introducer sheath configured to channel an implant assembly to the vessel, the implant assembly configured to seal a puncture hole created in a wall of the vessel.

In Example 14, the method of any one or any combination of Examples 1-13 can optionally be configured such that the guidewire defines a lumen and a length that is greater than a length of the dilator.

In Example 15, the method of Example 14 can optionally be configured such that the length of the guidewire is about 30 cm to about 80 cm, inclusive.

In Example 16, the method of any one or any combination of Examples 1-15 can optionally be configured such that the distal end of the guidewire extends at least about 10 cm within a lumen of the vessel after placement therein.

In Example 17, the method of any one or any combination of Examples 1-16 can optionally be configured such that an external diameter of the guidewire is about 0.01 inches to about 0.04 inches, inclusive.

In Example 18, the method of any one or any combination of Examples 1-17 can optionally be configured such that the vessel comprises a portion of the femoral artery.

In Example 19, the method of any one or any combination of Examples 1-18 can optionally be configured such that the vessel comprises a portion of the radial artery.

In Example 20, the method of any one or any combination of Examples 1-19 can optionally be configured such that a distance between an outer surface of a wall of the vessel and the skin of the patient is about 1 cm to about 10 cm.

In Example 21, the method of any one or any combination of Examples 1-20 can optionally be configured such that the dilator defines an external channel configured to slidably receive a channel guidewire.

In Example 22, the method of Example 21 can optionally be configured such that the method further involves inserting the channel guidewire into the external channel defined by the dilator.

In Example 23, the method of Example 22 can optionally be configured such that upon removing the first sheath, the channel guidewire remains inserted within the external channel defined by the dilator.

In Example 24, the method of Example 23 can optionally be configured such that passing the second sheath over the dilator and the guidewire further involves removing the channel guidewire from the external channel using the second sheath.

In Example 25, the method of Example 24 can optionally be configured such that removing the dilator and the guidewire further involves leaving the channel guidewire in place within the patient.

In Example 26, the method of any one or any combination of Examples 21-25 can optionally be configured such that a portion of the distal end of the dilator and a portion of a proximal end of the dilator are tapered and the external channel extends onto the distal and proximal ends.

In Example 27, the method of any one or any combination of Examples 21-26 can optionally be configured such that the guidewire and the channel guidewire are substantially equally dimensioned.

The scope of the present systems, devices, kits and methods should be determined with reference to the appended claims, along with the full scope of equivalents to which such claims are entitled. In the appended claims, the terms "including" and "in which" are used as the plain-English equivalents of the respective terms "comprising" and "wherein." Also in the following claims, the terms "including" and "comprising" are open-ended; that is, a system, kit or method that includes features or components in addition to those listed after such a term in a claim are still deemed to fall within the scope of that claim. Moreover, the terms "first," "second" and "third," etc. in the following claims are used merely as labels, and such terms not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
   positioning a distal end of a first sheath inside a vessel and a proximal end of the first sheath outside the skin of a patient;
   inserting a dilator over a guidewire and into the first sheath until a distal end of the dilator and a distal end of the guidewire are positioned inside the vessel, wherein the dilator defines an external channel configured to slidably receive a channel guidewire;
   inserting the channel guidewire into the external channel defined by the dilator;
   removing the first sheath, thereby leaving at least the dilator and the guidewire in place;
   passing a second sheath over at least the dilator and the guidewire until a distal end of the second sheath is positioned inside the vessel; and
   removing the dilator and the guidewire, thereby leaving at least the second sheath in place.

2. The method of claim 1, further comprising inhibiting patient blood loss through a puncture hole in a wall of the vessel using the combination of the dilator and the guidewire to substantially fill the puncture hole.

3. The method of claim 1, wherein the dilator is hubless and defines a lumen configured to receive the guidewire.

4. The method of claim 1, wherein the dilator comprises a middle portion having an approximately constant diameter, and wherein a portion of the distal end of the dilator and a proximal end of the dilator are tapered.

5. The method of claim 4, wherein one or more portions of the dilator include a radiopaque element.

6. The method of claim 1, wherein the dilator is about 30 cm to about 70 cm long, inclusive.

7. The method of claim 1, wherein the dilator comprises an approximately uniform stiffness profile along a length of the dilator.

8. The method of claim 1, wherein the second sheath is a sealing introducer sheath configured to channel an implant assembly to the vessel, the implant assembly configured to seal a puncture hole created in a wall of the vessel.

9. The method of claim 1, wherein the guidewire defines a lumen and a length that is greater than a length of the dilator.

10. The method of claim 9, wherein the length of the guidewire is about 30 cm to about 80 cm, inclusive.

11. The method of claim 1, wherein the distal end of the guidewire extends at least about 10 cm within a lumen of the vessel after placement therein.

12. The method of claim 1, wherein an external diameter of the guidewire is about 0.01 inches to about 0.04 inches, inclusive.

13. The method of claim 1, wherein upon removing the first sheath, the channel guidewire remains inserted within the external channel defined by the dilator.

14. The method of claim 13, wherein passing the second sheath over the dilator and the guidewire further comprises removing the channel guidewire from the external channel using the second sheath.

15. The method of claim 14, wherein removing the dilator and the guidewire further comprises leaving the channel guidewire in place within the patient.

16. The method of claim 1, wherein a portion of the distal end of the dilator and a portion of a proximal end of the dilator are tapered and the external channel extends onto the distal and proximal ends.

17. The method of claim 1, wherein the guidewire and the channel guidewire are substantially equally dimensioned.

* * * * *